(12) United States Patent
Raj et al.

(10) Patent No.: US 8,721,990 B2
(45) Date of Patent: May 13, 2014

(54) ASSAY DEVICE

(75) Inventors: Balbir Raj, Bedford (GB); Saji Eapen, Cambridge (GB); Ezra Linley, Cardiff (GB)

(73) Assignee: Alere Switzerland GmbH, Zug (CH)

(*) Notice: Subject to any disclaimer, the term of this patent is extended or adjusted under 35 U.S.C. 154(b) by 463 days.

(21) Appl. No.: 12/595,741

(22) PCT Filed: Apr. 9, 2008

(86) PCT No.: PCT/GB2008/001227
§ 371 (c)(1),
(2), (4) Date: Mar. 23, 2010

(87) PCT Pub. No.: WO2008/122796
PCT Pub. Date: Oct. 16, 2008

(65) Prior Publication Data
US 2010/0209297 A1    Aug. 19, 2010

(30) Foreign Application Priority Data

Apr. 10, 2007  (GB) .................................. 0706906.5
Sep. 1, 2007   (GB) .................................. 0717043.4

(51) Int. Cl.
| | | |
|---|---|---|
| *G01N 21/75* | (2006.01) | |
| *G01N 33/76* | (2006.01) | |
| *G01N 33/68* | (2006.01) | |
| *G01N 33/558* | (2006.01) | |

(52) U.S. Cl.
CPC .............. *G01N 33/76* (2013.01); *G01N 33/689* (2013.01); *G01N 33/558* (2013.01); *B01L 2300/0825* (2013.01); *B01L 2400/0406* (2013.01); *B01L 2300/087* (2013.01); *C12Q 2537/125* (2013.01)
USPC ........... 422/420; 422/400; 422/401; 422/421; 422/422; 422/423; 422/424; 422/425; 422/426; 422/427; 422/428; 422/429; 422/68.1; 422/82.05; 422/82.06; 436/164; 436/169; 436/170; 435/13; 435/283.1; 435/287.1; 435/287.7; 435/287.8; 435/287.9; 435/288.7

(58) Field of Classification Search
CPC ... G01N 33/558; G01N 33/689; G01N 33/76; B01L 2300/0825; B01L 2400/0406; B01L 2300/087; C12Q 2537/125
USPC ......... 422/400, 401, 420, 421, 422, 423, 424, 422/425, 426, 427, 428, 429, 68.1, 82.05, 422/82.06; 436/164, 169, 170; 435/13, 435/283.1, 287.1, 287.7, 287.8, 287.9, 435/288.7
See application file for complete search history.

(56) References Cited

U.S. PATENT DOCUMENTS

| | | | |
|---|---|---|---|
| 5,026,653 A | * | 6/1991 | Lee et al. ........................ 436/518 |
| 5,424,220 A | | 6/1995 | Goerlach-Graw et al. |

(Continued)

FOREIGN PATENT DOCUMENTS

| | | |
|---|---|---|
| DE | 202004008811 U1 | 9/2004 |
| EP | 291194 A1 | 11/1988 |

(Continued)

OTHER PUBLICATIONS

Office Action for Japanese Patent Application No. 2010-502562 dated Jun. 26, 2012.

(Continued)

*Primary Examiner* — Dennis M White
(74) *Attorney, Agent, or Firm* — Foley Hoag LLP

(57) ABSTRACT

Disclosed is an assay device for the determination of the presence and/or extent if an analyte in a liquid sample over an extended concentration range comprising a first assay and a second assay, wherein the first assay for an analyte comprises a first flow-path having a sole detection zone capable of immobilizing a labelled binding reagent and the second assay for said analyte comprises a second flow-path having a sole detection zone capable of immobilizing a labelled binding reagent, wherein the presence of labelled binding reagent at the detection zones provides an indication of the presence and/or extent of analyte in said liquid sample.

23 Claims, 4 Drawing Sheets

(56) References Cited

U.S. PATENT DOCUMENTS

| | | | |
|---|---|---|---|
| 5,707,818 A | 1/1998 | Chudzik et al. | |
| 5,731,212 A | 3/1998 | Gavin et al. | |
| 5,955,377 A | 9/1999 | Maul et al. | |
| 5,981,298 A | 11/1999 | Chudzik et al. | |
| 5,998,221 A | 12/1999 | Malick et al. | |
| 6,214,629 B1 | 4/2001 | Freitag et al. | |
| 6,297,020 B1 | 10/2001 | Brock | |
| 6,573,108 B1 | 6/2003 | Hardman et al. | |
| 6,656,745 B1 | 12/2003 | Cole | |
| 7,070,920 B2* | 7/2006 | Spivey et al. | 435/4 |
| 7,144,742 B2 | 12/2006 | Boehringer et al. | |
| 7,303,923 B2 | 12/2007 | Hardman et al. | |
| 7,315,378 B2 | 1/2008 | Phelan et al. | |
| 7,713,748 B2* | 5/2010 | Wei | 436/518 |
| 7,723,124 B2 | 5/2010 | Aberl et al. | |
| 7,989,217 B2 | 8/2011 | Yee et al. | |
| 2003/0207465 A1 | 11/2003 | Davis et al. | |
| 2004/0018576 A1 | 1/2004 | DeMatteo et al. | |
| 2004/0197820 A1 | 10/2004 | Wei et al. | |
| 2005/0036148 A1 | 2/2005 | Phelan | |
| 2005/0037510 A1 | 2/2005 | Sharrock et al. | |
| 2005/0112779 A1 | 5/2005 | Wei et al. | |
| 2005/0112780 A1 | 5/2005 | Song | |
| 2005/0130120 A1 | 6/2005 | Lambotte et al. | |
| 2005/0170527 A1* | 8/2005 | Boehringer et al. | 436/514 |
| 2005/0196812 A1 | 9/2005 | Williams | |
| 2005/0196875 A1 | 9/2005 | Blatt et al. | |
| 2005/0208593 A1 | 9/2005 | Vail et al. | |
| 2006/0019404 A1 | 1/2006 | Blatt et al. | |
| 2006/0024842 A1* | 2/2006 | Nylese | 436/514 |
| 2006/0199278 A1 | 9/2006 | Leclipteux et al. | |
| 2006/0246599 A1 | 11/2006 | Rosenstein et al. | |
| 2007/0020768 A1 | 1/2007 | Rundstrom et al. | |
| 2007/0042444 A1 | 2/2007 | Niskanen et al. | |
| 2007/0081920 A1 | 4/2007 | Murphy et al. | |
| 2007/0248983 A1 | 10/2007 | Schwind et al. | |
| 2009/0061534 A1 | 3/2009 | Sharrock | |

FOREIGN PATENT DOCUMENTS

| | | | |
|---|---|---|---|
| EP | 462376 | A2 | 12/1991 |
| EP | 0465266 | A1 | 1/1992 |
| EP | 0516095 | A2 | 12/1992 |
| EP | 1484601 | A2 | 12/2004 |
| EP | 1484641 | A1 | 12/2004 |
| EP | 1571451 | A1 | 9/2005 |
| GB | 2402474 | A | 12/2004 |
| JP | 04-351962 | A | 12/1992 |
| JP | 2004-361410 | A | 12/2004 |
| WO | WO-9706439 | A1 | 2/1997 |
| WO | WO-2004021004 | A1 | 3/2004 |

OTHER PUBLICATIONS

Office Action for U.S. Appl. No. 13/312,447 dated Sep. 6, 2012.

European Patent Office Communication for Application No. 08 736 903.9-2401 dated Feb. 2, 2012.

Anonymous, "Clearblue Digital Pregnancy Test with Conception Indicator," SPD Swiss Precision Diagnostics GmbH, pp. 1-7 (Jul. 31, 2008). [online] XP002540666 (Retrieved from the Internet: URL:http://www.swissprecisionadiagnostics.com/downloads/Conception_Indicator_Tech_Brochure_final.pdf>.

Creinin Mitchell, D., et al.; "Accuracy of serum beta-human chorionic gonadotropin cutoff values at 42 and 49 days' gestation," American Journal of Obstetrics and Gynecology, 185(4):966-969 (Oct. 2001).

Kadar, Nicholas, et al.; "A prospective, randomized study of the chorionic gonadotropin-time relationship in early gestation: Clinical implications," Fertility and Sterility, 60(3):409-412 (1993).

Lagrew, D.C., et al.; "Accuracy of Serum Human Chorionic Gonadotropin Concentrations and Ultrasonic Fetal Measurements in Determining Gestational Age," American Journal of Obstetrics and Gynecology, 149(2):165-168 (1984).

Lenton, E. A., et al.; "Plasma Concentrations of Human Chorionic Gonadotropin from the Time of Implantation Until the 2nd Week of Pregnancy," Fertility and Sterility, 37(6):773-778 (1982).

ISR for PCT/GB2008/001227 mailed Jun. 11, 2008.

ISR for PCT/GB2009/050619 mailed Sep. 9, 2009.

McChesney, Ruth, et al. "Intact HCG, free HCG β subunit and HCG β core fragment: longitudinal patterns in urine during early pregnancy," Human Reproduction, 20(4):928-935 (Jan. 21, 2005).

Sugantha et al. "Predictive value of plasma human chorionic gonadotropin following assisted conception treatment"; Human Reproduction; 15(2): 469-473 (2000).

Office Action in U.S. Appl. No. 12/987,503 dated Jul. 30, 2013.

Office Action in U.S. Appl. No. 12/996,197 dated Aug. 12, 2013.

Lopata, A., et al.; "Embryonic Development and Blastocyst Implantation Following In-Vitro Fertilization and Embryo Transfer," Fertility and Sterility, Elsevier Science Inc., New York, 38(6): 682-687 (Dec. 1, 1982).

Nepomnaschy, P. A. et al.; "Urinary hCG patterns during the week following implantation," Human Reproduction (Oxford), 23(2): 271-277 (Feb. 2008).

Wilcox, A. J., et al.; "Time of Implantation of the Conceptus and Loss Pregnancy," New England Journal of Medicine, 340(23): 1796-1799 (Jun. 10, 1999).

EP Office Action for Application No. 09 757 809.0 dated Jun. 25, 2012.

* cited by examiner

ASSAY DEVICE

RELATED APPLICATIONS

This application is a 371 national stage application of PCT/GB2008/001227, filed Apr. 9, 2008, which claims priority to Application No. GB 0706906.5, filed Apr. 10, 2007, and Application No. GB 0717043.4, filed Sep. 1, 2007. The entire contents of each of these applications are hereby expressly incorporated herein by reference.

FIELD OF THE INVENTION

The present invention relates to an assay device, kit and method for determining the presence or extent of an analyte over an extended concentration range.

BACKGROUND OF THE INVENTION

Simple lateral flow immunoassay devices have been developed and commercialised for detection of analytes in fluid samples, see for example EP291194. Such devices typically comprise a porous carrier comprising a dried mobilisable labelled binding reagent capable of binding to the analyte in question, and an immobilised binding reagent also capable of binding to the analyte provided at a detection zone downstream from the labelled binding reagent. Detection of the immobilised labelled binding at the detection zone provides an indication of the presence of analyte in the sample.

Alternatively, when the analyte of interest is a hapten, the immunoassay device may employ a competition reaction wherein a labelled analyte or analyte analogue competes with analyte present in the sample for an immobilised binding reagent at a detection zone. Alternatively the assay device may employ an inhibition reaction whereby an immobilised analyte or analyte analogue is provided at a detection zone, the assay device comprising a mobilisable labelled binding reagent for the analyte.

A sandwich immunoassay is often the assay of choice when detecting analytes. However, a sandwich assay is not always possible, for example in the case of small molecules such as haptens which may not be large enough to allow the simultaneous binding thereto of two different binding partners. A dose-response curve prepared using a typical lateral flow device employing a sandwich immunoassay shows increasing levels of signal with increasing analyte up to the point where at higher analyte levels the curve tends to plateau. At yet higher analyte levels, the signal begins to decrease due to preferential capture at the detection zone of analyte which has not yet bound to labelled reagent. This phenomenon is known as the hook effect. Thus sandwich immunoassays exhibit a limited assay range due to the fact that the signal amount or intensity observed at higher analyte levels may be the same, or even less, than that observed at lower analyte levels.

A competition or inhibition assay typically provides a high signal at zero or low levels of analyte. At increasing levels of analyte the signal level may still be high depending upon the amount of labelled binding species present compared to the amount of analyte. At still increasing levels of analyte, the signal starts to decrease as unbound analyte either competes with labelled analyte or analyte analogue for the immobilised binding reagent or binds to labelled binding reagent, lowering binding of the labelled binding reagent at the detection zone.

So, use of sandwich assays to measure analyte over an extended range may provide issues with respect to the hook effect. High analyte concentrations start producing a reduction in assay signal. Competition or inhibition assays result in the depletion in assay signal at high analyte concentrations and thus offer a limited range over which analyte can be measured.

Thus the above assay methods are not suitable for measuring levels of analyte over an extended analyte range.

US2005/0112780 discloses an assay device and method for extending the dynamic detection range of assay devices comprising a flow through porous carrier comprising a detection zone and a compensation zone provided downstream from the detection zone. The detection involves a first binding reagent which binds a detection probe to generate a detection signal having an intensity proportional to the amount of analyte, and the compensation zone comprises a second capture reagent which binds a detection probe to generate a signal which is inversely proportional to the intensity of the detection signal. The assay may further comprise a third calibration zone which generates a signal. The first binding reagent may be selected from a group including an antigen, hapten or streptavidin. The first and second binding reagents may be chosen from a number of species including an antigen, hapten or streptavidin.

US2004/0197820 discloses a flow through porous carrier assay device for reducing the hook effect comprising a detection zone wherein the device may include a downstream calibration zone.

US2006/0019404 discloses an assay device with an extended dynamic range comprising a lateral flow test-strip comprising a plurality of detection zones with a progressively decreased sensitivity to analyte concentration. The assay device may comprise two carriers each having a plurality of detection zones. The amount of label/signal present at the plurality of detection zones is detected to determine the analyte concentration.

EP462376 discloses an assay device comprising a capture site and a conjugate recovery site wherein the conjugate recovery site receives and binds said conjugate or conjugate complexes which migrate through said capture site and wherein immobilised conjugate at both the conjugate recovery site and capture site is detected to determine the amount of the analyte of interest.

The present inventors have shown that for assay devices wherein multiple detection zones for the detection of an analyte are provided on the same porous carrier, the binding at an upstream detection zone may change the binding characteristics at a downstream detection zone and that any variation in binding at an upstream detection zone may cause a compounded variation of binding at a downstream detection zone. This is especially so at higher analyte concentration levels and can give rise to poor assay precision. Furthermore, it has been found that cross-binding may occur between the respective binding reagents present in the detection zones during running of the test and cross-binding has also been observed during manufacture of the devices and whilst they are stored in the dry state. This was shown to have an impact on the levels of assay precision and sensitivity. These problems do not appear to have been recognised previously in the prior art.

It is an object to provide an improved assay device, kit and method for extending the analyte range of an assay.

SUMMARY OF THE INVENTION

According to a first aspect, the invention provides an assay device for the determination of the presence and/or extent of analyte in a liquid sample over an extended concentration range comprising a first assay and a second assay, wherein the first assay for an analyte comprises a first flow-path having a sole first assay detection zone capable of immobilising a labelled binding reagent and the second assay for said analyte comprises a second flow-path having a sole second assay detection zone capable of immobilising a labelled binding reagent, wherein the presence of the labelled binding reagent at the detection zones provides an indication of the presence and/or extent of analyte in said liquid sample.

The first assay may provide an indication of the level of analyte in a first concentration range and the second assay may provide an indication of the level of analyte in a second concentration range.

The first and second concentration ranges differ from each other. The first and second concentration ranges may overlap so as to provide a continuous concentration range.

The assay device may be capable of providing an indication of the level of analyte with respect to one or more thresholds. The assay device may provide an indication of the level of analyte below or above a plurality of thresholds. For example the number of thresholds may be two, three, four, five or greater. The assay device may comprise one or more stored threshold values, each stored value corresponding to a level of analyte.

The first and second assays may either independently or together provide an indication of the level of analyte within a certain range.

The first assay may provide an indication of the level of analyte of less than or equal to a first threshold and the second assay may provide an indication of the level of analyte of above a third threshold. The first and second assays together may provide an indication of the level of analyte of greater than or equal to the first threshold but less than the third threshold.

A binding reagent for the analyte or an analyte analogue may be provided in an immobilised form at a detection zone. The binding reagent may be chosen from a binding reagent for the analyte of interest, an analyte or analyte analogue, depending upon whether the assay is a sandwich type assay or a competition type assay. Similarly the labelled binding reagent may comprise a labelled binding reagent for the analyte of interest, a labelled analyte or labelled analyte analogue.

Alternatively a reagent may be provided in an immobilised form at a detection zone that is capable of binding a labelled binding reagent-analyte-second binding reagent complex. For example the second binding reagent may be provided in a mobilisable form and be conjugated or otherwise joined to a binding species such as biotin, the reagent immobilised at the detection zone being a complementary binding partner such as streptavidin or anti-biotin, such that an immobilised labelled binding reagent-analyte-second binding reagent complex-biotin-streptavidin complex is formed at the detection zone.

The second binding reagent may be provided in a mobilisable form which is capable of immobilising a labelled binding reagent-analyte complex at a detection zone. For example the second binding reagent may be attached to a particle such as agarose or white latex and the detection zone may comprise a filter of dimensions smaller than the particle, but larger than the size of the labelled binding reagent, such that the filter is able to trap the any labelled binding reagent-analyte-second binding reagent complex present, any labelled binding reagent that is not complexed to the capture reagent being able to pass through the filter.

The first and/or second assay may comprise a labelled binding reagent provided in a mobilisable form upstream from the first and/or second assay detection zone in the dry state prior to use of the device.

The first and second assays may each comprise a mobilisable labelled binding reagent provided upstream from an immobilised non-labelled binding provided at each detection zone.

The assay device may comprise more than two assays, each capable of detecting the analyte at a particular concentration range or above or below one or more thresholds.

The first and second assays may individually or together provide an indication of the particular level of analyte, or whether the analyte is above or below a certain threshold.

The assay device may have a common sample application region that fluidically connects the plurality of flow-paths. Thus a fluid sample applied to the common sample application region of the device is able to travel along the flow-paths of the respective assays to the respective detection zones.

As an alternative to providing the first and second assays within a single assay device, the assays may be provided as separate assay devices, the results from the respective devices when taken together being capable of providing an indication or measurement of the level of analyte.

Thus according to a second aspect, the invention provides an assay kit for the determination of the presence and/or extent of an analyte over an extended concentration range comprising a first assay device and a second assay device, wherein the first and second assay devices comprise respectively first and second assays according to the first aspect of the invention.

According to a third aspect, the invention provides a method for the determination of the presence and/or extent of an analyte over an extended analyte range comprising the steps of:
  a) adding a liquid sample to a first assay comprising a mobilisable labelled binding reagent provided upstream from a sole first assay detection zone and to a second assay comprising a mobilisable labelled binding reagent provided upstream from a sole second assay detection zone, said detection zones being capable of immobilising labelled binding reagent, and wherein detection of labelled reagent at the detection zones provides an indication of the extent and/or presence of an analyte in the liquid sample.
  b) reading the result of the assay.

In the case where the level of analyte is known to vary as a function of time, for example the pregnancy hormone hCG, the assay device may provide a time-based indication to the user, such as the extent of pregnancy in units of days or weeks.

The term "flow-path" for the purposes of this invention refers to a substrate that is able to convey a liquid from a first position to a second position and may be for example a capillary channel, a microfluidic pathway, or a porous carrier such as a lateral flow porous carrier. The porous carrier may comprise one or a plurality of porous carrier materials which may overlap in a linear or stacked arrangement or which are fluidically connected. The porous carrier materials may be the same or different. The first and second flow paths may be provided on separate substrates or they may be provided on a common substrate such that liquid being conveyed along a flow-path of the first assay is not able to cross over to the flow-path of the second assay. For example, the first and second assays may be provided on the same porous carrier such that the first and second flow-paths are isolated from each other. This may be achieved for example by laser cutting parts of the porous carrier to make it non-porous, thus separating the first and second flow-paths. As yet a further alternative, the first and second detection zones may be provided on the same flow-path in substantially a side by side arrangement, such that neither is provided downstream from the other.

In particular the flow-path may comprise a lateral flow porous carrier. The labelled binding reagents and detection zone of each assay may be provided respectively on different carrier materials. Suitable materials that may be employed as a porous carrier for providing the detection zone include nitrocellulose, acetate fibre, cellulose or cellulose derivatives, polyester, polyolefin or glass fibre. The porous carrier may comprise nitrocellulose. This has the advantage that a binding reagent can be immobilised firmly without prior chemical treatment. If the porous solid phase material comprises paper, for example, the immobilisation of the antibody in the second zone needs to be performed by chemical coupling using, for example, CNBr, carbonyldiimidazole, or tresyl chloride.

The assay may be provided in the form of an assay test-strip along which the liquid sample flows.

The term "binding reagent" refers to a member of a binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the specific binding pair are referred to as ligand and receptor (antiligand), a binding pair member and binding pair partner, and the like. A molecule may also be a binding pair member for an aggregation of molecules; for example an antibody raised against an immune complex of a second antibody and its corresponding antigen may be considered to be a binding pair member for the immune complex. The binding reagent may comprise an antibody or an antibody fragment, capable of binding to an antigen.

In addition to antigen and antibody binding pair members, other binding pairs include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), and the like. Furthermore, specific binding pairs can include members that are analogues of the original specific binding member.

"Label" when used in the context of a labelled binding reagent, refers to any substance which is capable of producing a signal that is detectable by visual or instrumental means. Various labels suitable for use in the present invention include labels which produce signals through either chemical or physical means, such as being optically detectable. Such labels include enzymes and substrates, chromogens, catalysts, fluorescent compounds, chemiluminescent compounds, electroactive species, dye molecules, radioactive labels and particle labels. The analyte itself may be inherently capable of producing a detectable signal. The label may be covalently attached to the binding reagent.

The label may comprise a particle such as gold, silver, colloidal non-metallic particles such as selenium or tellurium, dyed or coloured particles such as a polymer particle incorporating a dye, or a dye sol. The dye may be of any suitable colour, for example blue. The dye may be fluorescent. Dye sols may be prepared from commercially-available hydrophobic dyestuffs such as Foron Blue SRP (Sandoz) and Resolin Blue BBLS (Bayer). Suitable polymer labels may be chosen from a range of synthetic polymers, such as polystyrene, polyvinyltoluene, polystyrene-acrylic acid and polyacrolein. The monomers used are normally water-insoluble, and are emulsified in aqueous surfactant so that monomer micelles are formed, which are then induced to polymerise by the addition of initiator to the emulsion. Substantially spherical polymer particles are produced. According to an exemplary embodiment the label is a blue polymeric particle.

The liquid sample can be derived from any source, such as an industrial, environmental, agricultural, or biological source. The sample may be derived from or consist of a physiological source including blood, serum, plasma, interstitial fluid, saliva, sputum, ocular lens liquid, sweat, urine, milk, mucous, synovial liquid, peritoneal liquid, transdermal exudates, pharyngeal exudates, bronchoalveolar lavage, tracheal aspirations, cerebrospinal liquid, semen, cervical mucus, vaginal or urethral secretions and amniotic liquid. In particular the source is human and in particular the sample is urine.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof.

In particular the analyte is human chorionic gonadotropin (hCG). The analyte may have a sole binding region or epitope or may have more than one binding region. For example the analyte hCG comprises an alpha sub-unit identical to that of luteinising hormone (LH), follicle stimulating hormone (FSH) and thyroid stimulating hormone (TSH) and a beta sub-unit unique to hCG. Antibodies to the alpha and beta sub-units may be used to bind to hCG in a sandwich immunoassay format.

The assay device of the invention may be used to measure the extent or presence of hCG over an extended concentration range. The range may vary from between about 10 mIU/ml to about 250,000 mIU/ml.

According to an embodiment, the device is able to measure the amount of hCG in the fluid sample and to indicate to the user, based upon stored reference values the extent of pregnancy in time based units. The device may also indicate whether the subject is pregnant or not, determined by whether the level of hCG is above or below a base threshold. The reference and threshold values are typically stored within the device as part of an algorithm. The base threshold may typically range from 10-25 mIU/ml.

According to an embodiment, the first assay may provide either an indication of whether the subject is pregnant or not, based upon whether the level of hCG detected is respectively above or below a base threshold, and/or if pregnant, the level of hCG in a first range of less than or equal to a first threshold, the second assay provides an indication of the level of hCG in a second range of above or equal to a second threshold and wherein the first and second assays together provide an indication of the level of hCG in a third range of greater than the first threshold but less than the second threshold.

The first and/or second assay may further comprise a control zone to indicate that the assay test has been carried out satisfactorily, namely the reagents were present in the test device and that they become mobilised during running the test and have been transported along the flow path. The control zone can also indicate that the reagents within the device are capable of immunochemical interactions, confirming the chemical integrity of the device. This is important when considering the storage and shipment of the device under desiccated conditions within a certain temperature range. The control zone is typically positioned downstream from the detection zone and may for example comprise an immobilised binding reagent for a labelled binding reagent. The labelled binding reagent may be present in a mobilisable form upstream from the control zone and detection zone. The labelled binding reagent may be the same or different to the labelled binding reagent for the analyte.

The assay device may comprise a porous sample receiver in fluid connection with and upstream from the first and second flow-paths. The porous sample receiver may be common to both assays. Thus a fluid sample applied to the common sample application region of the device is able to travel along the flow-paths of the respective assays to the respective detection zones. The porous sample receiver may be provided within the housing or may at least partially extend out of said housing and may serve for example to collect a urine stream. The porous sample receiver may act as a fluid reservoir. The porous sample receiving member can be made from any bibulous, porous or fibrous material capable of absorbing liquid rapidly. The porosity of the material can be unidirectional (i.e. with pores or fibres running wholly or predominantly parallel to an axis of the member) or multidirectional (omnidirectional, so that the member has an amorphous sponge-like structure). Porous plastics material, such as polypropylene, polyethylene (preferably of very high molecular weight), polyvinylidene fluoride, ethylene vinylacetate, acrylonitrile and polytetrafluoro-ethylene can be used. Other suitable materials include glass-fibre.

If desired, an absorbent "sink" can be provided at the distal end of the carrier material. The absorbent sink may comprise of, for example, Whatman 3MM chromatography paper, and should provide sufficient absorptive capacity to allow any unbound labelled binding reagent to wash out of the detection zone. As an alternative to such a sink it can be sufficient to have a length of porous solid phase material which extends beyond the detection zone.

Following the application of a binding reagent to a detection zone, the remainder of the porous solid phase material may be treated to block any remaining binding sites. Blocking can be achieved by treatment for example with protein (e.g. bovine serum albumin or milk protein), or with polyvinylalcohol or ethanolamine, or combinations thereof. To assist the free mobility of the labelled binding reagent when the porous carrier is moistened with the sample, the porous carrier may further comprise a sugar such as sucrose or lactose and/or other substances, such as polyvinyl alcohol (PVA) or polyvinyl pyrrolidone (PVP). Such material may be deposited for example as an aqueous solution in the region to which the labelled binding reagent is to be applied. Such materials could be applied to the porous carrier as a first application followed by the application of the label, alternatively such materials could be mixed with the label and applied to the porous carrier or combinations of both. Such material may be deposited upstream from or at the labelled binding reagent.

Alternatively, the porous carrier may not be blocked at the point of manufacture; instead the means for blocking the porous carrier are included in a material upstream from the porous carrier. On wetting the test strip, the means for blocking the porous carrier are mobilised and the blocking means flow into and through the porous carrier, blocking as the flow progresses. The blocking means include proteins such as BSA and casein as well as polymers such as PVP, PVA as well as sugars and detergents such as Triton-X100. The blocking means could be present in the macroporous carrier material.

The nitrocellulose porous carrier may have having a pore size of at least about 1 micron, for example greater than about 5 microns, and for example about 8-12 microns.

The nitrocellulose porous carrier may be backed e.g. with a plastics sheet, to increase its handling strength. This can be manufactured easily by forming a thin layer of nitrocellulose on a sheet of backing material such as Mylar®.

The dried binding reagents may be provided on a porous carrier material provided upstream from a porous carrier material comprising the detection zone. The upstream porous carrier material may be macroporous. The macroporous carrier material should be low or non-protein-binding, or should be easily blockable by means of reagents such as BSA or PVA, to minimise non-specific binding and to facilitate free movement of the labelled reagent after the macroporous body has become moistened with the liquid sample. The macroporous carrier material can be pre-treated with a surface active agent or solvent, if necessary, to render it more hydrophilic and to promote rapid uptake of the liquid sample. Suitable materials for a macroporous carrier include plastics materials such as polyethylene and polypropylene, or other materials such as paper or glass-fibre. In the case that the labelled binding reagent is labelled with a detectable particle, the macroporous body may have a pore size at least ten times greater than the maximum particle size of the particle label. Larger pore sizes give better release of the labelled reagent. As an alternative to a macroporous carrier, the labelled binding reagent may be provided on a non-porous substrate provided upstream from the detection zone, said non-porous substrate forming part of the flow-path.

The first and/or second assays may comprise a glass-fibre macroporous carrier provided upstream from and overlapping at its distal end a nitrocellulose porous carrier.

The assay device or kit may further comprise one or more means to determine the extent and/or amount of labelled species present. For example, an optical means comprising an optical detection means such as a photodetector and one or more light sources such as an LED positioned so as to optically illuminate the detection zones to determine the extent and/or amount of labelled species present. The assay device may further comprise one or more of a power source, a computation means, a signal transduction means, an algorithm, a display means, a memory means and data in/out port. The assay device may comprise a housing which serves to house the first and second assays as well as other components of the device. The device may comprise stored threshold values.

The assay device typically comprises a housing containing the assays. The housing may be fluid impermeable and constructed from a suitable plastics material, such as ABS. The assay may further comprise a sample receiving member for receiving the fluid sample. The sample receiving member may extend from the housing.

The housing may be constructed of a fluid impermeable material. The housing will also desirably exclude ambient light. The housing or casing will be considered to substantially exclude ambient light if less than 10%, preferably less than 5%, and most preferably less than 1%, of the visible light incident upon the exterior of the device penetrates to the interior of the device. A light-impermeable synthetic plastics material such as polycarbonate, ABS, polystyrene, polystyrol, high density polyethylene, or polypropylene containing an appropriate light-blocking pigment is a suitable choice for use in fabrication of the housing. An aperture may be provided on the exterior of the housing which communicates with the assay provided within the interior space within the housing. Alternatively the aperture may serve to allow a porous sample receiver to extend from the housing to a position external from the housing.

The first and second assays may be provided for example in a side by side arrangement or in a face to face arrangement wherein one assay is provided above the other. The device may comprise a single photodetector to detect both detection zones.

In addition to measuring the detection zones of the respective assays as well as the control zones where present, the optical means may also measure a reference zone, namely a portion of the flow-path which is free from binding reagent in the dry state.

The purpose of the reference zone is to provide a signal value against which the signal value obtained at the detection zone may be compared. Measurement of the reference zone enables measurement of the background levels of reflected or transmitted light from the flow-path. The background level may be due for example to the optical reflectance of the porous carrier, the presence of liquid sample, or of components of the assay such as a labelled binding reagent. The levels of light measured at the detection zone may therefore be corrected with respect to the levels of background light to provide a compensated signal indicative of the amount of labelled binding reagent present at the detection zone. Measurement at the reference zone may also compensate for any variation between fluid samples applied to assay devices, for example urine samples may vary widely in colour.

An assay device for measuring the level of analyte in a liquid sample may comprise an optical detection means arranged to measure the intensity of light reflected from a detection zone, control zone and reference zone of an assay device. The optical means may comprise one or more light sources such as an LED and one or more photo detectors.

The assay will typically take place over a time during which labelled binding reagent accumulates at the test and control zones. A typical time for an assay test for the determination of hCG in urine is 3 minutes. The assay test time may be started automatically, for example when liquid sample is determined by the optics as having reached a portion of the flow-path or porous carrier.

A suitable light source is an LED. The colour of the LED will be determined by the colour of the labelled binding reagent. For a blue label, a suitable colour for the LED is red. The LED may be illuminated at a particular frequency or frequencies in order to illuminate a particular zone of the assay device. Light is reflected or transmitted from the zone onto a photodetector which records an electrical signal. The number of electrical signals recorded will depend upon the operating frequency of the LED and thus one or more signals may be recorded over time. The signals will typically be expressed as a % absorbance (% A). The signal may be determined after the full time for the assay test or it may be determined early, for example after having crossed a particular signal threshold.

Each measurement zone is typically illuminated by a single LED. A photodetector may detected light from one than one measurement zone and therefore reflected light from one than one LED. This may be achieved by carrying out the illumination process sequentially such that device is able to know which from which zone light is being reflected from onto the photodetector. The sequential illumination process may be repeated with a fixed or varied frequency during the duration of the assay such that the levels of signal over time at each zone may be monitored. The assay strips may be positioned in a side by side arrangement and the photodetector and light sources positioned above the plane of the strips such that the detection control and reference zones are positioned towards the light sources and optical detectors.

The device may comprise a means to detect the addition of flow to the assay device. For example, the change in levels of light detected from one or more zones may be monitored to determine whether and when a fluid sample has been applied to the device. The timing of the assay test may be started automatically for example when liquid sample has reached a particular zone.

The device may comprise a flow control means wherein the change in levels of light detected from one or more zones may be used to determine whether and when a fluid sample has been applied to the device and to determine the flow-rate of liquid sample along the device by measurement of flow between one or more measured zones. Determination of the flow-rate may be used as a further quality control check, for example the assay may be rejected if the flow-rate is either greater than or less than set levels. The computation circuit may be responsive to the signals to calculate a flow rate for a fluid flowing along the carrier, compare the calculated flow rate to upper and lower limits, and reject the assay result if the calculated flow rate is outside the upper and lower limits.

The typical optical detection system will comprise at least one light source and at least one photodetector (such as a photodiode). Preferred light sources are light emitting diodes or LEDs. Reflected light and/or transmitted light may be measured by the photodetector. For the purposes of this disclosure, reflected light is taken to mean that light from the light source is reflected from the porous carrier or other liquid transport carrier onto the photodetector. In this situation, the detector is typically provided on the same side of the carrier as the light source. Transmitted light refers to light that passes through the carrier and typically the detector is provided on the opposite side of the carrier to the light source. For the purposes of a reflectance measurement, the carrier may be provided with a backing such as a white reflective MYLAR® plastic layer. Thus light from the light source will fall upon the carrier, some will be reflected from its surface and some will penetrate into the carrier and be reflected at any depth up to and including the depth at which the reflective layer is provided. Thus, a reflectance type of measurement may actually involve transmission of light through at least some of the thickness of the porous carrier.

The assay device will typically comprise one or more apertures or windows through which light may shine from the one of more sources of illumination onto a particular zone of the assay or assay strip. The windows serve to define the area of light falling onto a particular zone and to define which part of the assay or assay strip is illuminated. Each zone to be illuminated may have a corresponding window. Thus a device having four measurement zones will have four windows. Light reflected from the windows is collected by the one or more photodetectors. For an assay device comprising a flow path having a plurality of zones the time taken for the liquid sample to travel between the zones may be measured.

Measurements of the light reflected from each window may be taken periodically (for example approximately twice a second) and a low pass digital filter may be used to reject noise and smooth the data. Filtered values may be used for detecting flow and determining the assay result.

For each window, a ratio may be calculated of the measured value when the particular measurement zone in the flow-path is dry ("calibration value"), namely before any liquid sample has reached said zone, divided by the measured value when the measurement zone is wet and a line may have developed. This ratio equals the proportion of light reflected after the change in the reflective properties of the flow-path as a consequence of the liquid sample passing along the flow-path. For example when the flow-path comprises a porous carrier such as nitrocellulose the change in reflective properties can be quite marked.

For each window, the window ratio at the reference, control, and test windows is equal to the measured value when the porous carrier is dry, t=0 (prior to addition of sample), divided by the measured value at time t after addition of sample:

For each time point t the window ratios for each window may be evaluated as follows:

$$Ref\ ratio_t = \frac{\text{filtered reference window } value_{time=0}}{\text{filtered reference window } value_{time=t}}$$

$$Test\ ratio_t = \frac{\text{filtered test window } value_{time=0}}{\text{filtered test window } value_{time=t}}$$

$$Ctrl\ ratio_t = \frac{\text{filtered } Ctrl \text{ window } value_{time=0}}{\text{filtered } Ctrl \text{ window } value_{time=t}}$$

Calculation of Filtered % A Values

For each time point, t, % A values may calculated using these ratios for a test line and a control line using the reference ratio as a baseline for the background that would have occurred in all windows had a line not developed.

$$Test_t(\%\ A) = \frac{Ref\ ratio_t - test\ ratio_t}{Ref\ ratio_t} \times 100\%$$

$$Ctrl_t(\%\ A) = R\frac{ef\ ratio_t - Ctrl\ ratio_t}{Ref\ ratio_t} \times 100\%$$

The assay device may comprise a stored control threshold (CLT) wherein if the value of signal determined for the control <CLT, the result will be rejected due to insufficient development of the control line and if said value >CLT the control will be determined to be satisfactory.

According to an embodiment the assay device may comprise two assay test-strips each comprising a porous carrier, wherein one assay is a high sensitivity (HS) assay, namely the assay is sensitive to levels of analyte at a low analyte concentrations, and a low sensitivity (LS) assay, namely the assay is sensitive to analyte at higher analyte concentrations. In particular the analyte is hCG.

The assay device may comprise two test (detection) zones, each assay test-strip comprising a test zone, a reference zone and a control zone. Signals may be measured at both the HS and LS zones and may be defined as follows:

$$HSratio_t = \frac{\text{filtered } HS \text{ test window } value_{time=0}}{\text{filtered } HS \text{ test window } value_{time=t}}$$

$$LSratio_t = \frac{\text{filtered } LS \text{ test window } value_{time=0}}{\text{filtered } LS \text{ test window } value_{time=t}}$$

The filtered % A values may be defined for the HS and LS zones as follows:

$$HS_t(\%\ A) = \frac{Ref\ ratio_t - HS\ test\ ratio_t}{Ref\ ratio_t} \times 100\%$$

$$LS_t(\%\ A) = \frac{Ref\ ratio_t - LS\ test\ ratio_t}{Ref\ ratio_t} \times 100\%$$

The normalised percentage relative attenuation (% A) is given by the difference of the reference (ref.) window ratio and the window ratio being considered (control or test windows) divided by the reference window ratio and multiplied by 100%.

Typically the % A values will be those obtained at the full assay development time (FDT)

Flow Detection and Validation

Flow Detection

The window ratio for each window may be used to detect the flow of fluid past the window. Flow is classed as having reached a window when the ratio has dropped by the Flow Detection Threshold Percentage (FDT %). This corresponds to an increase in the filtered value over its calibration value by the same proportion.

$$\text{For time } t, \text{ Window ratio} \geq \frac{1}{1 + FDT\ \%}$$

$$\frac{\text{filtered } value_{time=t}}{\text{filtered } value_{time=0}} \geq 1 + FDT\ \%$$

or

The time for each window when the criterion is first satisfied is recorded for flow validation.

Flow Validation

Various parameters corresponding to flow may be stored within the device and used to classify flow of liquid sample along porous carrier of an assay device. The device may display any errors in flow as a consequence of using the device.

The device may comprise one or more of a stored minimum flow detection time (Min FDT), a maximum flow detection time (Max FDT), a minimum window transit time (Min MTT) and a flow detection threshold (FDT).

The device may comprise a number of stored threshold values such as the control line threshold. Values above or at this threshold may be determined as being a valid control and values below this threshold may be determined as being a non-valid control, namely the test will be rejected.

The assay device may further comprise one or more stored measurement overflow parameters, wherein if any of the measurements is greater or much less than a value that would have been expected, the result will be rejected. This enables the assay device to reject for example, hardware failures such as a break or shorting in the circuit board, a flat battery, a blocked optical window, a failed LED and so on.

The assay device may comprise a further threshold, for example an early decision threshold (EDT), wherein if the signal exceeds that threshold at any time during the test, an early result is given, namely earlier than the nominal time taken for the test to run (the full signal development time) In the case of an hCG measurement, an indication of pregnant will be given by the display means. The assay device may further comprise a stored value corresponding to a minimum development time (MDT) wherein the assay device will only provide an early result once the MDT has been exceeded.

The various stored threshold values may be stored in the device as part of one or more algorithms.

According to an embodiment an assay device is provided for the detection of hCG analyte in urine wherein the device comprises:

an optical illumination and detection means for illuminating and detecting labelled binding reagent at the detection zones, a computation means for calculating a level of hCG or a value corresponding to the level of hCG, a display means for displaying a result of the assay test, a stored base threshold value, wherein a level of hCG corresponding to a value below the stored base threshold is indicative of being not pregnant and wherein a level of hCG corresponding to a value at or above the stored base threshold is indicative of being pregnant, two further first and second stored threshold values wherein a level of hCG corresponding to a value above the base threshold value but less than or equal to a first threshold value is indicative of a level of pregnancy in a first range, a level of hCG corresponding to a value above the base threshold and greater than the second threshold is indicative of a level of pregnancy in a third range, and a level of hCG corresponding to a value above the base threshold and greater or equal to the first threshold but less than the second threshold is indicative of a level of hCG in a third range, wherein the display means is capable of indicating either a not pregnant condition, or a pregnant condition and the extent of pregnancy.

The first assay differs from the second assay such that the respective assays are capable of measuring analyte at different levels.

For example the first and second assays may employ differing assay architectures, such as the first assay employing a sandwich binding reaction and the second assay employing a competition or inhibition reaction. The first assay may comprise a mobilisable labelled binding reagent for the analyte provided upstream from a detection zone, said detection zone comprising a non-labelled immobilised binding reagent for the analyte and the second assay may comprise a mobilisable binding reagent for the analyte provided upstream from an immobilised non-labelled binding reagent for the mobilisable binding reagent. Alternatively the second assay may comprise a mobilisable labelled analyte or analyte analogue reagent provided upstream from an immobilised non-labelled binding reagent for the analyte or analyte analogue. For example, the sandwich assay may be the high sensitivity assay, namely it is capable of measuring analyte at a lower concentration range and the inhibition or competition assay may be a low sensitivity assay, namely it is capable of measuring analyte at a higher concentration range.

The assay device may for example comprise first and second assays wherein the non-labelled binding reagent of the first assay differ from the non-labelled binding reagent of the second assay, and/or the labelled binding reagent of the first assay differs from the labelled binding reagent of the second assay. For example this may be a difference in concentration, or a difference in affinity for an analyte, analyte analogue or binding reagent. A high affinity binding reagent will have a higher analyte sensitivity than a lower affinity binding reagent. Similarly a low concentration of binding reagent will have a lower analyte sensitivity than a high concentration of binding reagent. The first and second assays may be varied in this way such that they are capable of determining an analyte at different concentration ranges.

Thus the assay device may comprise a high analyte sensitivity first assay comprising a mobilisable labelled binding reagent of a certain concentration or affinity provided upstream from a detection zone and a low analyte sensitivity second assay comprising a mobilisable labelled binding reagent having a lower concentration or affinity provided upstream from a detection zone. Alternatively or additionally, the first assay comprising an immobilised binding reagent at a detection zone of a certain concentration or affinity and a second assay may comprise an immobilised binding reagent at a detection zone having a lower concentration or affinity.

The assay sensitivity can be manipulated by altering the ratio of binding reagent to the label. If a particle is used as a label, then the quantity of the binding reagent applied to the label can be altered. A further lever to manipulate the sensitivity of an assay is to vary the quantity of the label used in the assay. For example the sensitivity of an assay may be lowered by reducing the ratio of binding reagent to labelled species for the labelled binding reagent. Thus the assay device may comprise a first high analyte sensitivity assay and a second low analyte sensitivity assay wherein the first assay comprises a mobilisable particle labelled binding reagent provided upstream from a detection zone having a ratio of binding reagent to particle label and wherein the second assay comprises a mobilisable particle labelled binding reagent provided upstream from a detection zone having a lower ratio of binding reagent to particle label than that of the first assay.

A further means of manipulating the sensitivity of an assay is to alter the optical density of a label. The assay sensitivity can be lowered by use of a label with a low optical density. This may be achieved for example by provision of a polymer particle label having a low concentration of dye or by use a coloured label which is less sensitive to an optical detector. Thus the assay device may comprise a first high analyte sensitivity assay and a second low analyte sensitivity assay wherein the first assay comprises a mobilisable particle labelled binding reagent provided upstream from a detection zone, said label having an optical density and wherein the second assay comprises a mobilisable particle labelled binding reagent provided upstream from a detection zone wherein the label has a lower optical density than that of the first assay.

Yet a further way to measure high analyte levels is to employ a non-particulate labelled binding reagent. High levels of analyte when measured by way of a sandwich binding assay require high levels of binding reagent. In the case wherein the label is a particle label, provision of high levels of analyte within or on the porous carrier can give rise to steric hindrance resulting in poor assay sensitivity. Conversely, at lower analyte levels, the use of a non-particle labelled binding reagent can give rise to a low signal due to the low optical density. However, at high analyte levels, non-particle labels may be present at sufficiently high levels to be readily detected. Therefore the assay may comprise a first high analyte sensitivity assay comprising an optically detectable particle labelled binding reagent provided upstream from a detection zone and a second low analyte sensitivity assay comprising an optically detectable non-particulate labelled binding reagent provided upstream from a detection zone. An example of a optically detectable non-particulate label may be a dye. The dye may be fluorescent.

Assay sensitivity may be influenced by the flow rate of the porous carrier. A way to lower the sensitivity of the assay is to employ a porous carrier (such as nitrocellulose) having a higher flow rate. Thus the assay device may comprise a first high analyte sensitivity assay having a porous carrier having a flow-rate and a second low analyte sensitivity assay having a porous carrier having a higher or faster flow rate than that of the first assay.

The sensitivity of an assay may additionally or alternatively be manipulated by modifying the rate at which the labelled binding reagent is released from its origin. A further way to lower analyte sensitivity is to provide for a rapid release of the labelled binding reagent from the porous carrier during contact with the liquid sample. The release of the labelled binding reagent can be modified by the provision of sugars, proteins or other polymeric substances such as methylcellulose within the device. Such substances may be provided in the vicinity of the binding reagents or upstream from them.

Use of a Scavenger Reagent

A further way to lower the analyte sensitivity is to provide a scavenger binding reagent to bind to the analyte. The scavenger binding reagent may be provided upstream from a detection zone and may be immobilised, mobilisable or both. The scavenger binding reagent may be provided at either the same region of the porous carrier as the mobilisable binding reagent, upstream from it or downstream from it. The scavenger binding reagent may bind to the same binding region of the analyte as the mobilisable labelled binding reagent or to a different region of the analyte than the labelled binding reagent. Either or both of the assays may employ a scavenger binding reagent and the scavenger binding reagents may differ from one another in terms of their concentration, affinity or both.

For the purpose of this application the term scavenger binding reagent denotes an additional binding reagent capable of binding analyte and the term "scavenger" is used merely to distinguish the binding reagents from the other binding reagents present in the device. The scavenger binding reagent is typically unlabelled.

According to an embodiment, the assay device comprises a first assay comprising a first porous carrier comprising a mobilisable labelled binding reagent provided upstream from a detection zone and a second assay comprising a mobilisable labelled binding reagent provided upstream from a detection zone and a scavenger binding reagent also provided upstream from the detection zone of the second assay. The first assay may be the high analyte sensitivity assay and the second assay may be the low analyte sensitivity assay.

The scavenger reagent may be provided in a mobilisable form.

The scavenger reagent may have a different affinity for the analyte than the mobilisable labelled binding reagent of the second assay. In an exemplary embodiment, the scavenger binding reagent has a higher affinity for the analyte than the mobilisable binding reagent of the second assay. The amount scavenger binding reagent may be varied to change the sensitivity of the second assay to analyte concentration. Increasing the amount of scavenger binding reagent present lowers the sensitivity of the assay due to the fact that the scavenger binding reagent is able to bind more analyte, effectively lowering the proportion of labelled binding reagent that is able to bind to the detection zone. The amount of labelled binding reagent in the first and second assays may be varied. Increasing the amount of labelled binding reagent has the tendency to reduce the hook effect and the amount of labelled binding reagent present, especially in the lower sensitivity assay, may be varied depending upon the analyte range.

The scavenger binding reagent may be capable of binding to the same or a different region on the analyte. In an exemplary embodiment, the scavenger binding reagent is capable of binding to a different binding region of the analyte. In particular where the analyte to be determined is hCG, the scavenger binding reagent is capable of binding to the beta-subunit, and the mobilisable labelled binding reagent is capable of binding to the alpha-subunit.

According to an exemplary embodiment, the assay device comprises a first assay comprising a glass-fibre porous carrier material comprising a mobilisable particle-labelled binding reagent for an analyte and a nitrocellulose porous carrier material provided downstream from the glass-fibre porous carrier material having a detection zone comprising a immobilised binding reagent for the analyte and a second assay comprising a glass-fibre porous carrier material comprising a mobilisable particle-labelled binding reagent for a first binding region of the analyte and mobilisable scavenger binding reagent for a second binding region of the analyte and a nitrocellulose porous carrier material provided downstream from the glass-fibre porous carrier material having a detection zone comprising an immobilised binding reagent for the second binding region of the analyte.

It will be appreciated that the above ways to alter the assay sensitivity of an assay are not exhaustive and further might be used in combination. The assay device may comprise one or more of the above features to affect assay sensitivity. The particular assay architecture chosen would depend upon the analyte and its concentration range.

For the avoidance of doubt it is hereby expressly stated that any feature described herein as "preferred", "desirable", "advantageous" or the like may be present in the invention in isolation, or in any combination with any other feature so described, unless the context dictates otherwise.

Aspects of the invention are further illustrated by reference to the following figures.

COMPARATIVE EXAMPLE 1

Figure 1:
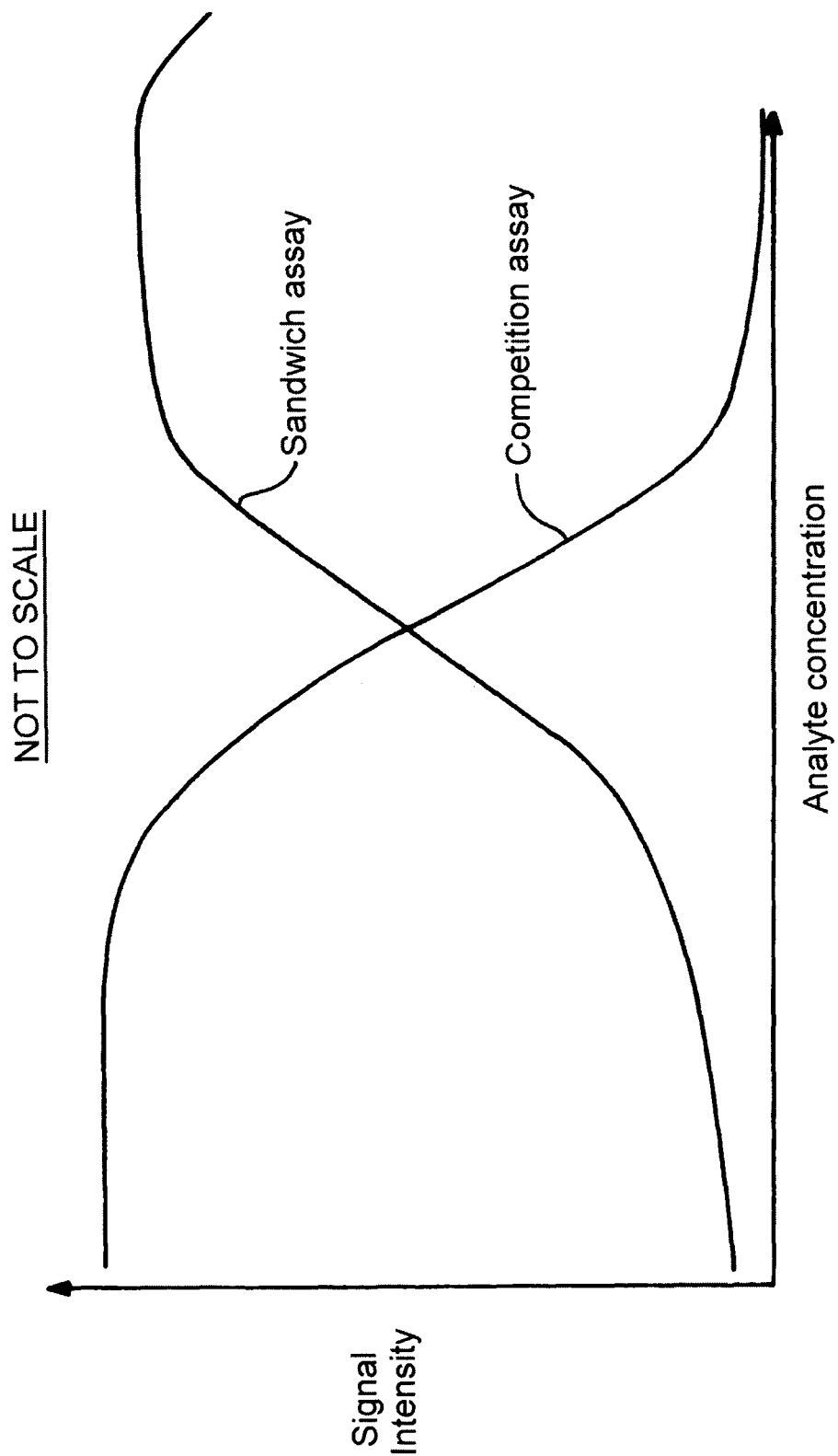
FIG. 1 illustrates typical signal responses that are observed for a typical assay compared with that of a typical competition assay.

Preparation of an Assay Device Comprising a Single Porous Carrier Comprising a First Upstream Detection Zone for a Sandwich Assay and a Second Downstream Detection Zone for an Inhibition Assay An assay test-strip comprising a first upstream detection zone for a sandwich assay and the second downstream detection zone for an inhibition assay and a mobilisable labelled binding reagent provided upstream from said zones was prepared as follows:

Preparation of the Downstream Detection Zone

A solution of 1.5 mg/ml mouse anti-β-hCG (in-house clone 3468) in PBSA buffer and 7.2 KIU/ml hCG (Scipac) in PBSA/ovalbumin was mixed for 1-hour to provide an anti-β hCG-hCG conjugate. The resulting conjugate was deposited as a line onto bands of nitrocellulose of dimensions 350 mm length×40 mm width (Whatman, having a pore-size of 8 microns and a thickness between 90-100 microns which had been laminated to a 175 micron backing layer). The conjugate produced above was dispensed as a line ~1.2 mm in width and ~300 mm in length at a rate of 1 µl/cm being 16 mm from the end of the band of nitrocellulose. using a Biodot xyz3050 dispensing platform. This formed the second downstream detection zone for an inhibition assay.

Preparation of the Upstream Detection Zone

The first detection zone for a sandwich assay (upstream detection zone) was prepared by dispensing a line of anti-β-hCG antibody (in-house clone 3468) at a concentration of 3 mg/ml in PBSA buffer, at a rate of 1 µl/cm on the same band of nitrocellulose to which the anti-β hCG-hCG conjugate had been applied. The anti-β-hCG antibody was applied using the Biodot xyz3050 dispensing platform as a line ~1.2 mm in width and ~300 mm in length 10 mm from the same end of the band of nitrocellulose to which the anti-β hCG-hCG conjugate had been applied.

The bands of NC were dried using Hedinair drying oven serial #17494 set at 55° C. and speed 5 (single pass).

The NC was then blocked using a blocking buffer comprising a mixture of 5% ethanol (BDH Analar 104766P) plus 150 mM Sodium Chloride (BDH Analar 10241AP) plus 50 mM trizma base from (Sigma T1503) plus XX Tween 20 (Sigma P1379) and 1% (w/v) polyvinyl alcohol (PVA, Sigma 360627).

The blocking buffer was applied at a rate of 1.75 μl/mm to the proximal end of the band. Once the blocking solution had soaked into the membrane a solution of 2% (w/v) sucrose (Sigma S8501 in deionised water) was applied using the same apparatus at a rate of 1.6 μl/mm and allowed to soak into the nitrocellulose membrane for ~5 minutes).

The bands of NC were then dried using a Hedinair drying oven serial #17494 set at 75° C. and speed 5 (single pass).

Preparation of the Labelled Binding Reagent.

Labelled Binding Reagent was Prepared According to the Following Protocol:
Coating Latex Particles with Anti-α hCG
1. Dilute blue latex particles from Duke Scientific (400 nm in diameter, DB1040CB at 10% solids (w/v)) to 2% solids (w/v) with 100 mM di-sodium tetra borate buffer pH 8.5 (BDH AnalaR 102676G) (DTB).
2. Wash the diluted latex by centrifuging a volume of (2 mls) of diluted latex in two Eppendorf centrifuge tubes at 17000 rpm (25,848 rcf) for 10 minutes on an Heraeus Biofuge 17RS centrifuge. Remove and discard the supernatant and re-suspend the pellets in 100 mM DTB to give 4% solids (w/v) in a total volume of 1 ml.
3. Prepare a mixture of ethanol and sodium acetate (95% Ethanol BDH AnalaR 104766P with 5% w/v Sodium Acetate Sigma S-2889).
4. Add 100 μls ethanol-sodium acetate solution to the washed latex in step 2 (this is 10% of the volume of latex).
5. Dilute the stock antibody (in-house clone 3299) to give ~1200 μg/ml antibody in DTB.
6. Heat a volume of 1 ml of the diluted antibody from step 5 in a water bath set at 41.5° C. for ~2 minutes. Also heat the washed latex plus ethanol-sodium acetate from step 4 in the same water bath for 2 minutes.
7. Add the diluted antibody to the latex plus ethanol-acetate, mix well and incubate for 1 hour in the water bath set at 41.5° C. whilst mixing using a magnetic stirrer and a magnetic flea placed in the mixture.
8. Prepare 40 mg/ml Bovine Serum Albumin (BSA) Solution (Intergen W22903 in de-ionised water). Block the latex by adding an equal volume of 40 mg/ml BSA to the mixture of latex/antibody/ethanol-acetate and incubate in the water bath at 41.5° C. for 30 minutes with continued stirring.
9. Centrifuge the mixture at 17000 rpm for 10 minutes as in step 2, (split the volume into 1 ml lots between Eppendorf tubes). Remove and discard the supernatant and re-suspend the pellet in 100 mM DTB. Repeat the centrifugation as in step 2, remove and discard the supernatant and re-suspend in pellet in Air Brushing Buffer (20% (w/v) Sucrose Sigma S8501, 10% BSA (w/v) in 100 mM Trizma Base Sigma T1503 pH to 9). Add Air Brushing Buffer to give 4% solids (w/v) latex.

The conjugated latex was and sprayed in a mixture of BSA and sucrose onto a glass-fibre porous carrier (F529-09, Whatman) at a rate of 50 g/hr and 110 mm/s and dried using a Hedinar Conveyor Oven Serial number 17494 set at 65° C. and speed 5 (single pass).

The glass fibre material with sprayed latex was attached to the nitrocellulose membrane using a clear adhesive coated laminate film (Ferrisgate, 38 mm wide) arranged such that the sprayed latex was uppermost and the glass fibre overlapped the surface of the nitrocellulose by ~2 mm along the length (350 mm) of the band of nitrocellulose membrane. The glass fibre was attached to the end of the nitrocellulose such that the upstream of the upstream first detection zone.

The laminated sheet was subsequently cut into test-strips of 6 mm width.

EXAMPLE 1

Assay devices were prepared in a similar manner to that of Comparative Example 1 except that the first and second detection zones were provided on respectively first and second test-strips, wherein the first and second detection zones were provided on nitrocellulose, each test-strip comprising glass-fibre sprayed with mobilisable latex labelled a-hCG antibody provided upstream from the nitrocellulose. The first and second detection zones were each provided on the nitrocellulose test-strips at the 16 mm position.
Running the Test Strips The test-strips according to Example 1 and Comparative Example 1 were tested using in-house readers with calibrated hCG buffer standards at concentrations 0, 25 50, 100, 250, 500, 1000, 2500, 5000, 10000, 15000, 20000, 25000, 50000, 150000, 200000 and 250000 mIU/ml hCG.

Figure 2:
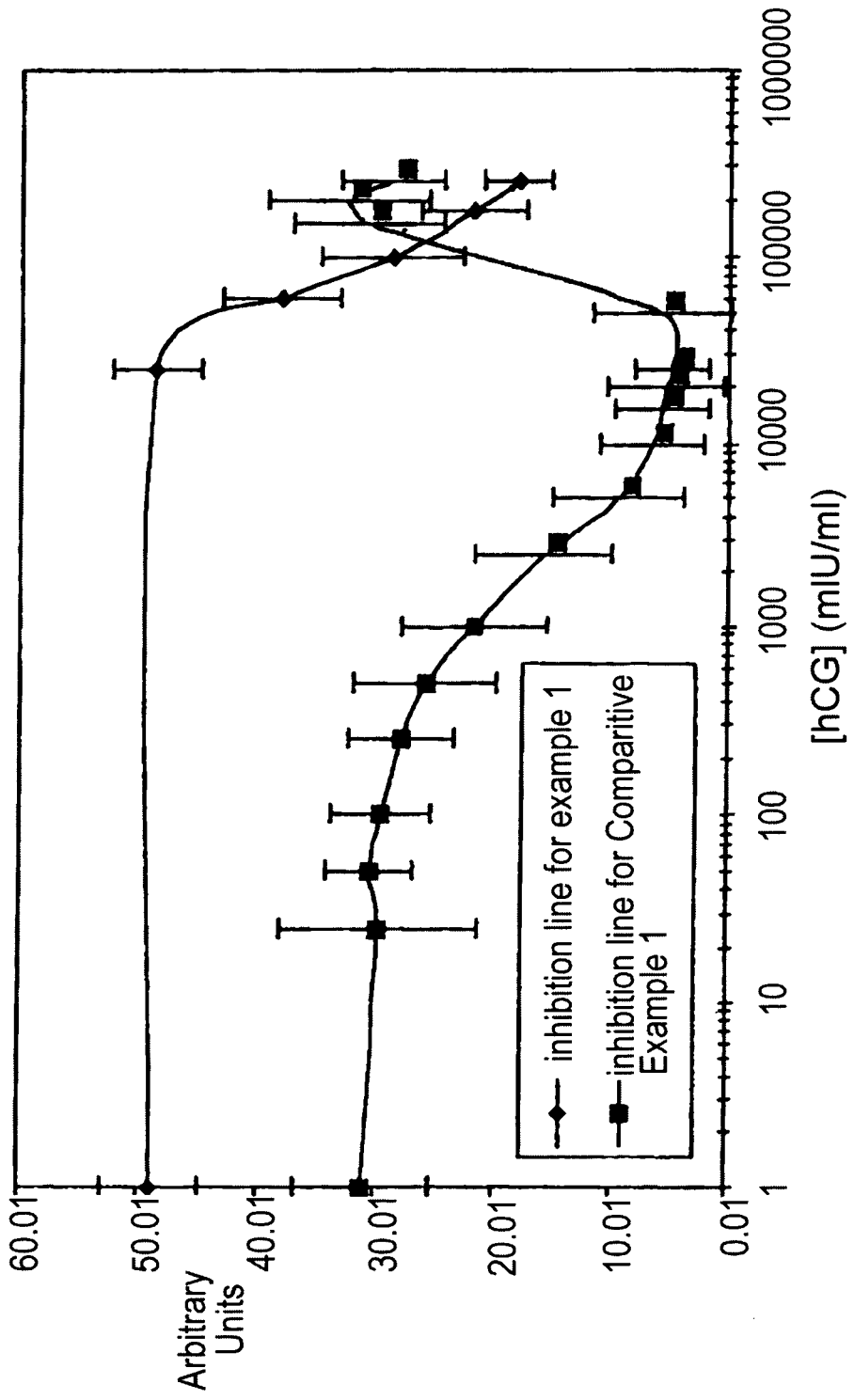
FIG. 2 illustrates plots of signal intensity vs. hCG concentration for Example 1 and Comparative Example 1.

The signal intensity measured at the inhibition detection zones as a function of hCG concentration of the assays of example 1 (denoted by --◆--) and comparative example 1 (denoted by --■--) is shown in FIG. 2 as signal in arbitrary units vs. mIU/ml hCG.

As can be seen from this Figure, the inhibition detection zone of Comparative Example 1 shows an initial plateau at levels of hCG ranging from 0-100 mIU/ml, followed by a decrease in the intensity at higher levels of hCG as expected. However, at higher levels still, the signal intensity was observed to increase. By comparison, the signal intensity of Example 1 decreases at higher hCG levels without the subsequent increase in signal intensity at higher hCG levels. As can be seen, the inhibition zone of assay device constructed according to Comparative Example 1 has a more limited range over which hCG may be measured.

EXAMPLE 2

Preparation of Assay Devices Comprising a First Test-Strip Comprising a First Sandwich Assay and a Second Test-Strip Comprising a Scavenger Reagent in Addition to a Sandwich Assay Preparation of the First Assay Test-Strip The first assay test strip was prepared according to the first (sandwich) assay test-strip according to that of Example 1.

Preparation of the Second Assay (Scavenger) Test-Strip

The detection zone was prepared on nitrocellulose using the preparation according to that of the first assay test-strip of Example 2.

Mouse-anti-human α-hCG mAb (clone 3299) conjugated to 400 nm blue polystyrene latex (Duke Scientific) was mixed with scavenger antibody mAb mouse anti-human β-hCG (in-house clone 3468) at 3 mg/ml to give a final % blue latex of 3%, a final 3468 concentration of 0.075 mg/ml and 0.06 mg/ml concentration of the free anti-β hCG antibody. The resulting mixture was airbrushed onto Whatman glass fibre (F529 25 mm wide reels) using the BIODOT XYZS (serial number 1673) at 90 g/hr sprayed at 2.02 μg/cm onto F529-09 glass fibre.

The glass fibre was dried using a Hedinar Conveyor Oven Serial number 17494 set at 65° C. and speed 5 (single pass). A second pass of latex was deposited onto the glass fibre by repeating the above however at an offset of ~0.8 mm from the original position of spray (further downstream of the glass fibre). The glass fibre as dried as described above.

COMPARATIVE EXAMPLE 2

Assay devices constructed wherein both detection zones were provided on the same porous carrier were not able to result in the measurement of an analyte concentration over an extended analyte range.

Assay devices according to Example 2 were tested using in-house detection zone optical readers with calibrated hCG buffer standards at 12 concentrations ranging from 0-250000 mIU/ml hCG. 10 replicates per concentration level were measured giving a total number of 120 assay devices that were tested.

Figure 3:
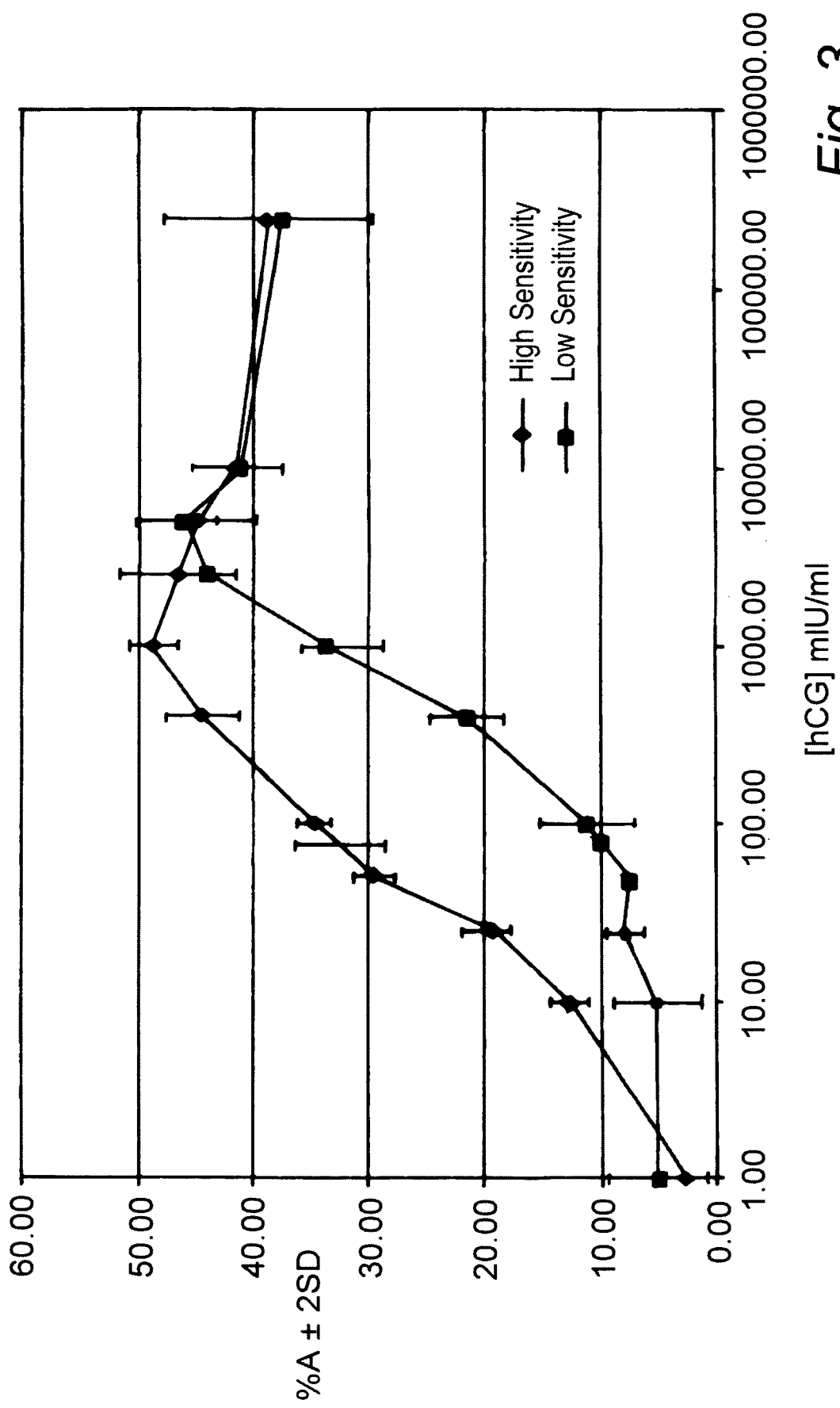
FIG. 3 illustrates a plot of signal intensity vs. hCG concentration for the assay device according to Example 2.

The signal intensity vs. hCG concentration for the second assay constructed according to Example 2 is shown in FIG. 3.

The first assay test-strip according to Example 2 was able to determine the amount of hCG present up to about 400 mIU/ml before the assay curve flattened off. The second assay test-strip according to Example 2 was able to detect hCG levels of greater than about 1000 mIU/ml. Measurement of the signals at both the first and second assay test-strips enabled determination of the level of hCG between about 400 mIU/ml and 1000 mIU/ml.

The Effect of Varying the Amounts of Scavenger Antibody

Second assay test-strips according to Example 2 were prepared except the amount of scavenger antibody present was varied during preparation of the strip to give a final 3468 concentration of 0.12, 0.16, 0.2 and 0.24 mg/ml.

Figure 4:
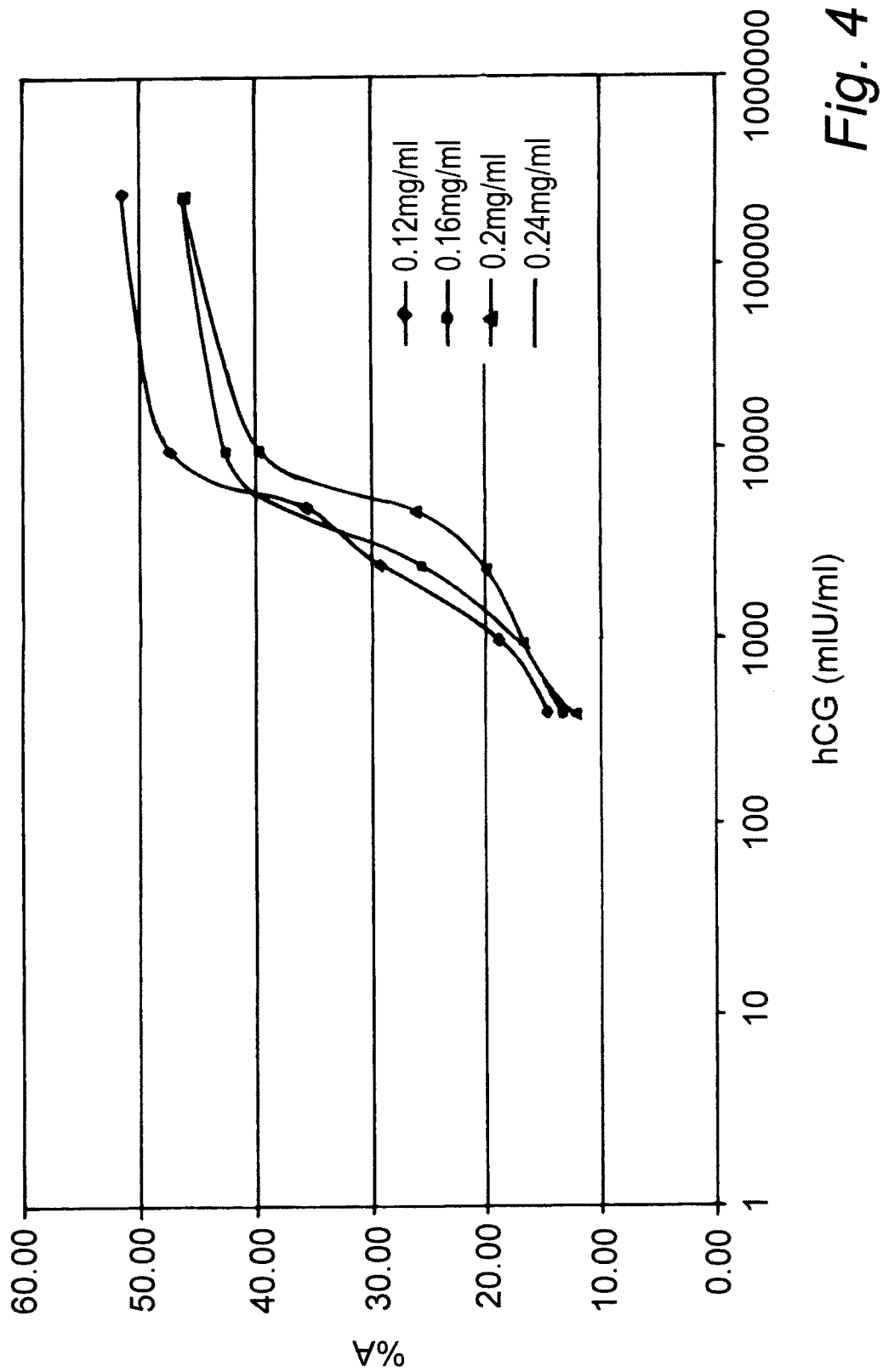
FIG. 4 illustrates the effect of varying the amounts of scavenger antibody for the assay device according to Example 2.

As can be seen from FIG. 4 increasing the amount of scavenger antibody lowers the amount of analyte captured at the detection zone.

The invention claimed is:

1. An assay device for the determination of hCG in a liquid sample over an extended concentration rang, comprising a first assay and a second assay,
wherein the first assay comprises a first flow-path having a sole first assay detection zone and a mobilisable, labeled, hCG-binding reagent provided upstream from the first assay detection zone; and the second assay comprises a second flow-path having a sole second assay detection zone, a mobilisable, labeled, hCG-binding reagent provided upstream from the second assay detection zone, and a mobilisable scavenger binding reagent for hCG provided upstream from the second assay detection zone;
wherein the first and second assay detection zones each independently comprise an immobilised reagent that is capable of immobilising the respective labeled, hCG-binding reagent in the presence of hCG;
wherein said first and second assays are provided on separate substrates, or on a common substrate but with the first and second flow-paths fluidically isolated from one another;
wherein the immobilisation of the labeled, hCG-binding reagents at the detection zones provides an indication of hCG in said liquid sample; and wherein the first assay provides an indication of hCG in a first concentration range and the second assay provides an indication of hCG in a second, higher concentration range.

2. The device according to claim 1 wherein the first and/or second flow-path comprises a porous carrier.

3. The device according to claim 2 wherein the porous carrier is a lateral flow porous carrier.

4. The device according to claim 1 wherein for the second assay, the scavenger binding reagent has a higher binding affinity for hCG than the mobilisable, labeled, hCG-binding reagent.

5. The device according to claim 1 wherein the mobilisable, labeled, hCG-binding reagent and the scavenger binding reagent of the second assay bind to respectively a first and second binding region of hCG, and the second assay detection zone comprises an immobilised binding reagent for a second binding region of hCG.

6. The device according to claim 1 wherein the mobilisable, labeled, binding reagent and the scavenger binding reagent of the second assay are provided in the same region.

7. The device according to claim 1 wherein the labelled binding reagent is labelled with an optically detectable particle.

8. The device according to claim 1, comprising a common porous sample receiver.

9. The assay device according to claim 1, wherein the first assay is a high sensitivity assay and the second assay is a low sensitivity hCG assay.

10. The device according to claim 1, comprising a housing wherein the first and second assays are provided within said housing.

11. The device according to claim 1 for the detection of hCG analyte in urine wherein the device comprises:
a) an illumination and detection means for illuminating and detecting labelled binding optical reagent at the detection zones;
b) a computation means for calculating a level of hCG or a value corresponding to the level of hCG;
c) a display means for displaying a result of the assay test;
d) a stored base threshold value, wherein a level of hCG corresponding to a value below the stored base threshold is indicative of being not pregnant and wherein a level of hCG corresponding to a value at or above the stored base threshold is indicative of being pregnant;
e) two further first and second stored threshold values wherein a level of hCG corresponding to a value less than or equal to a first threshold value is indicative of a level of pregnancy in a first range, a level of hCG corresponding to a value greater than the second threshold is indicative of a level of pregnancy in a third range, and a level of hCG corresponding to a value greater or equal to the first threshold but less than the second threshold is indicative of a level of hCG in a second range, wherein the display means is capable of indicating either a not pregnant condition, or a pregnant condition and the extent of pregnancy.

12. The device according to claim 1, wherein the scavenger binding reagent is unlabelled.

13. The device according to claim 1, wherein the scavenger binding reagent of the second assay is capable of binding to the beta subunit of hCG, and the mobilisable, labeled, hCG-binding reagent of the second assay is capable of binding to the alpha subunit of hCG.

14. The device according to claim 1, which is for the determination of the extent of pregnancy of a subject in time based units.

15. The device according to claim 14, wherein the extent of pregnancy is determined in units of weeks.

16. The device according to claim 14, wherein the determination of the extent of pregnancy is based upon stored reference values.

17. The device according to claim 1, wherein said extended concentration range is the range of about 10 to about 250,000 mIU/ml hCG.

18. The device according to claim 1, which does not contain more than two hCG assays.

19. The device according to claim 1, wherein the immobilised reagents in the first and second assay detection zones are immobilised hCG-binding reagents.

20. The device according to claim 19, wherein the immobilised reagents in the first and second assay detection zones are independently streptavidin or anti-biotin.

21. The device according to claim 1, wherein the first and second concentration ranges overlap.

22. A method of determining the extent of pregnancy in a pregnant woman subject, the method comprising the step of analysing a urine sample from the subject using an assay device in accordance with claim 1.

23. A method of determining pregnancy as well as the extent of pregnancy in a pregnant woman subject, the method comprising the step of analysing a urine sample from the subject using an assay device in accordance with claim 1.

* * * * *

UNITED STATES PATENT AND TRADEMARK OFFICE
CERTIFICATE OF CORRECTION

PATENT NO.         : 8,721,990 B2                                       Page 1 of 1
APPLICATION NO.    : 12/595741
DATED              : May 13, 2014
INVENTOR(S)        : Balbir Raj et al.

It is certified that error appears in the above-identified patent and that said Letters Patent is hereby corrected as shown below:

In the Claims

In Claim 1, at column 19, line number 52 should read,

--sample over an extended concentration rang[e], comprising a--

Signed and Sealed this
Fourteenth Day of October, 2014

Michelle K. Lee
*Deputy Director of the United States Patent and Trademark Office*

UNITED STATES PATENT AND TRADEMARK OFFICE
CERTIFICATE OF CORRECTION

| | |
|---|---|
| PATENT NO. | : 8,721,990 B2 |
| APPLICATION NO. | : 12/595741 |
| DATED | : May 13, 2014 |
| INVENTOR(S) | : Balbir Raj et al. |

It is certified that error appears in the above-identified patent and that said Letters Patent is hereby corrected as shown below:

In the Claims

In Claim 1, at column 19, line number 52 should read,

--sample over an extended concentration range, comprising a--

This certificate supersedes the Certificate of Correction issued October 14, 2014.

Signed and Sealed this
Tenth Day of March, 2015

Michelle K. Lee
*Deputy Director of the United States Patent and Trademark Office*